(12) United States Patent
Suekane et al.

(10) Patent No.: US 10,352,861 B2
(45) Date of Patent: Jul. 16, 2019

(54) OBSERVATION ASSISTANCE DEVICE AND FLUORESCENCE OBSERVATION SYSTEM

(71) Applicant: OLYMPUS CORPORATION, Tokyo (JP)

(72) Inventors: Asuka Suekane, Tokyo (JP); Shintaro Takahashi, Tokyo (JP); Kentaro Imoto, Tokyo (JP); Atsushi Doi, Tokyo (JP); Shinichi Takimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/215,809

(22) Filed: Dec. 11, 2018

(65) Prior Publication Data

US 2019/0113459 A1 Apr. 18, 2019

Related U.S. Application Data

(63) Continuation of application No. PCT/JP2016/069467, filed on Jun. 30, 2016.

(51) Int. Cl.
*G01N 21/64* (2006.01)
(52) U.S. Cl.
CPC ..... *G01N 21/6458* (2013.01); *G01N 21/6428* (2013.01); *G01N 2201/12* (2013.01)
(58) Field of Classification Search
CPC ........... G01N 21/6458; G01N 21/6428; G01N 2201/12
See application file for complete search history.

(56) References Cited

U.S. PATENT DOCUMENTS

2005/0215911 A1 9/2005 Alfano et al.
2005/0270639 A1* 12/2005 Miki ................... G02B 21/0088
359/381

(Continued)

FOREIGN PATENT DOCUMENTS

EP 2273301 A1 1/2011
EP 2778659 A1 9/2014

(Continued)

OTHER PUBLICATIONS

International Search Report dated Sep. 20, 2016 issued in PCT/JP2016/069467.

*Primary Examiner* — Marcus H Taningco
(74) *Attorney, Agent, or Firm* — Scully, Scott, Murphy & Presser, P.C.

(57) ABSTRACT

An observation assistance device of the present invention includes: an information storage unit that stores sample state information showing a sample state change, a type of sample, a type of fluorescent substance, and an observation condition in fluorescence observation performed on a predetermined sample, and under a predetermined observation condition; an input unit via which inputs the type of sample to be observed and the type of fluorescent substance to be used; an assistance-display generating unit that reads sample state information and an observation condition of fluorescence observation performed on the same type of sample as the type of sample input, using the same type of fluorescent substance as the type of fluorescent substance, and generates an assistance display showing the sample state information in relation to the two or more parameters included in the observation condition; and a display unit that displays the generated assistance display.

9 Claims, 6 Drawing Sheets

(56) References Cited

U.S. PATENT DOCUMENTS

| | | | |
|---|---|---|---|
| 2007/0201130 A1 | 8/2007 | Fujinoki et al. | |
| 2010/0103255 A1* | 4/2010 | Nishiwaki | G06K 9/0014 |
| | | | 348/79 |
| 2011/0036993 A1 | 2/2011 | Mano et al. | |
| 2012/0305803 A1* | 12/2012 | Foelling | G01N 21/6458 |
| | | | 250/459.1 |
| 2014/0247976 A1 | 9/2014 | Suzuki | |

FOREIGN PATENT DOCUMENTS

| | | |
|---|---|---|
| JP | 2005-331889 A | 12/2005 |
| JP | 2007-209219 A | 8/2007 |
| JP | 2007-525261 A | 9/2007 |
| JP | 2009-162708 A | 7/2009 |
| JP | 2013-050666 A | 3/2013 |
| JP | 2013-104674 A | 5/2013 |
| WO | WO 2005/069887 A2 | 8/2005 |
| WO | WO 2009/104718 A1 | 8/2009 |

* cited by examiner

FIG. 3

CELL TYPE: CELL A
FLUORESCENT SUBSTANCE: FLUORESCENT SUBSTANCE A

- ☐ LIGHT SOURCE INTENSITY _____ W (DURING MEASUREMENT)
- ☐ OBJECTIVE LENS _____ (IRRADIATION FIELD _____ cm²)
- ☐ FILTER _____ (WAVELENGTH WIDTH _____ nm)
- ☐ IRRADIATION POWER DENSITY _____ W/cm²
- ☐ DURATION OF EXPOSURE _____ sec
- ☐ NUMBER OF IMAGE ACQUISITIONS _____ NUMBER OF TIMES
- ☑ TOTAL IRRADIATION TIME _____ sec
- ☐ IRRADIATION ENERGY (SINGLE) _____ J/cm²
- ☐ IRRADIATION ENERGY (TOTAL) _____ J/cm²
- ☑ IMAGE ACQUISITION INTERVAL _____ min
- ☐ FLUORESCENT SUBSTANCE CONCENTRATION _____ mol/L

OBSERVATION ASSISTANCE DEVICE AND FLUORESCENCE OBSERVATION SYSTEM

CROSS-REFERENCE TO RELATED APPLICATIONS

This is a continuation of International Application PCT/JP2016/069467, with an international filing date of Jun. 30, 2016, which is hereby incorporated by reference herein in its entirety.

TECHNICAL FIELD

The present invention relates to an observation assistance device and a fluorescence observation system.

BACKGROUND ART

When a sample is repeatedly irradiated with intense excitation light intermittently but for a relatively long time, as in time-lapse fluorescence observation of a sample using a microscope, a known microscope measures the cumulative time over which the excitation light is radiated, and, when the cumulative time exceeds a predetermined reference value, issues a notification to that effect or shuts off the excitation light for the purpose of reducing invasion of the sample with the excitation light (for example, see Japanese Unexamined Patent Application, Publication No. 2005-331889).

SUMMARY OF INVENTION

An aspect of the present invention is an observation assistance device including: an information storage unit that is configured to store, in an associated manner, sample state information showing a sample state change, a type of sample, a type of fluorescent substance, and an observation condition in fluorescence observation performed on a predetermined sample, using a predetermined fluorescent substance, and under a predetermined observation condition including two or more parameters; an input unit via which a user inputs the type of sample to be observed and the type of fluorescent substance to be used; an assistance-display generating unit that is configured to generate an assistance display showing the sample state information on the basis of the type of sample and the type of fluorescent input in the input unit; and a display unit that is configured display the assistance display generated by the assistance-display generating unit, wherein the assistance-display generating unit includes a one or more processor, the processor is configured to read, from the information storage unit, sample state information and an observation condition of fluorescence observation performed on the same type of sample as the type of sample input in the input unit, using the same type of fluorescent substance as the type of fluorescent substance input in the input unit, and generates the assistance display in relation to the two or more parameters included in the observation condition.

Another aspect of the present invention is a fluorescence observation system including: an image acquisition unit that is configured to acquire a fluorescence image under a prescribed observation condition, on a predetermined sample, and using a predetermined fluorescent substance; and any one of the observation assistance devices described above.

BRIEF DESCRIPTION OF DRAWINGS

FIG. 3 shows an example screen shown by the observation assistance device in FIG. 1, via which observation conditions are input and parameters are selected.

DESCRIPTION OF EMBODIMENTS

An observation assistance device 1 and a fluorescence observation system 100 according to an embodiment of the present invention will be described below with reference to the drawings.

Figure 1:
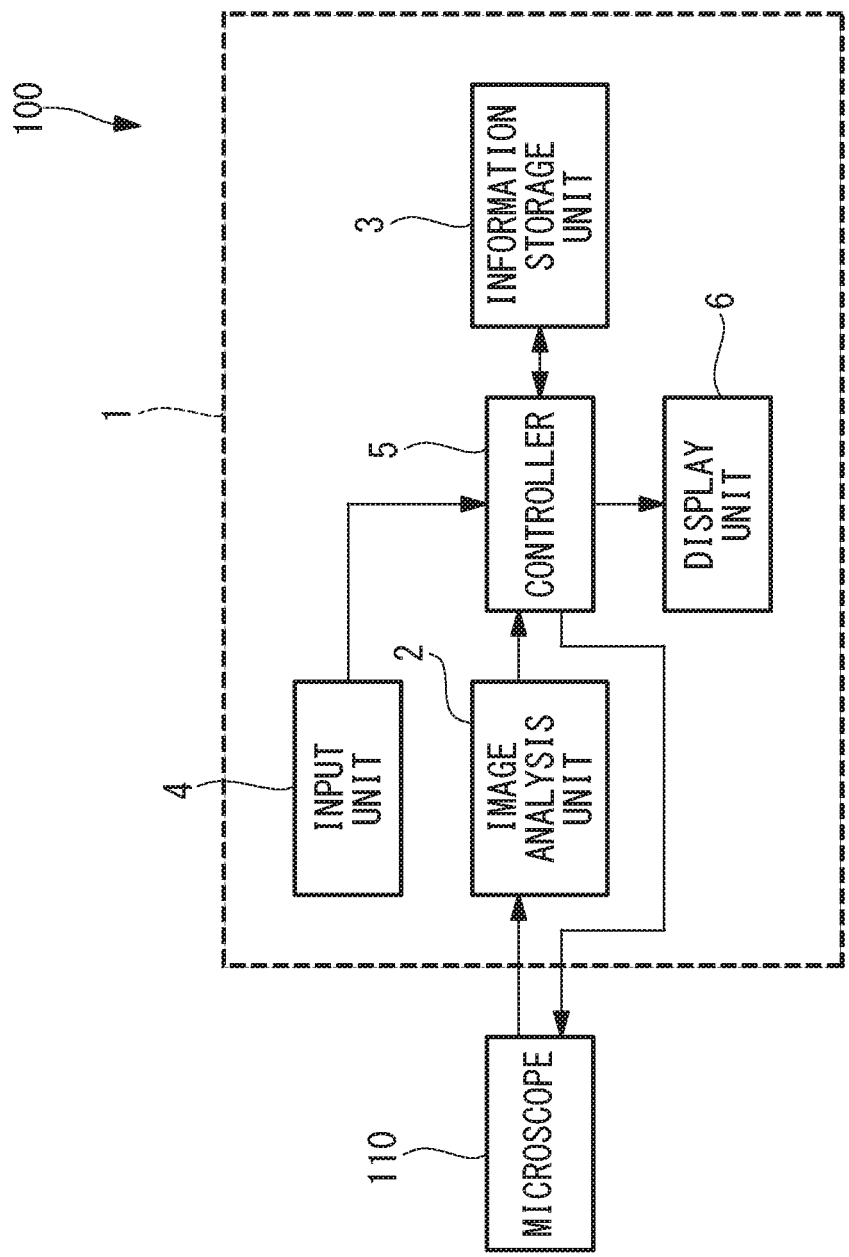
FIG. 1 shows the overall configuration of a fluorescence observation system having an observation assistance device according to an embodiment of the present invention.

As shown in FIG. 1, the fluorescence observation system 100 according to this embodiment includes a microscope (image acquisition unit) 110 that performs fluorescence observation of a prescribed sample, using a prescribed fluorescent substance, and under prescribed observation conditions to acquire fluorescence images, and the observation assistance device 1 according to this embodiment.

The microscope 110 acquires two or more fluorescence images using an observation method such as, for example, time-lapse observation, in which, for example, image acquisition is performed twice or more at certain intervals in single fluorescence observation.

As shown in FIG. 1, the observation assistance device 1 according to this embodiment includes: an image analysis unit 2 that calculates sample state information showing a state change of a sample during fluorescence observation on the basis of two or more fluorescence images acquired by the microscope 110 in each fluorescence observation; an information storage unit 3 that stores the sample state information calculated by the image analysis unit 2 in association with the type of the sample, the type of the fluorescent substance, and the observation conditions used in the fluorescence observation; an input unit 4 via which a user inputs the type of sample and the type of fluorescent substance; a controller (assistance-display generating unit) 5 that reads, from the information storage unit 3, observation conditions and sample state information corresponding to the type of sample and the type of fluorescent substance input via the input unit 4 and generates an assistance display; and a display unit 6 that displays the generated assistance display.

More specifically, the image analysis unit 2 calculates the cell growth rate, serving as the sample state information, by counting the number of cells, serving as the samples, from fluorescence images acquired at certain intervals, for example, fluorescence images acquired at the beginning and the end of each fluorescence observation. Any information that shows a state change of the cells, which indicates whether or not the cells have been damaged during the fluorescence observation, such as the cell survival rate, the cell doubling time, and the cell movement amount, may be used as the sample state information.

The controller 5: reads observation conditions and sample state information corresponding to the input sample type and fluorescent substance type from the information storage unit 3; forms a two-dimensional map (heat map) in which two preliminarily set parameters in the parameters contained in the observation conditions, for example, the single radiation energy and the image-capturing interval in fluorescence observation, are used as the two coordinate axes, generating a distribution of the respective observation conditions; and generates an assistance display that shows sample state information corresponding to each observation condition in an associated manner.

Figure 2:
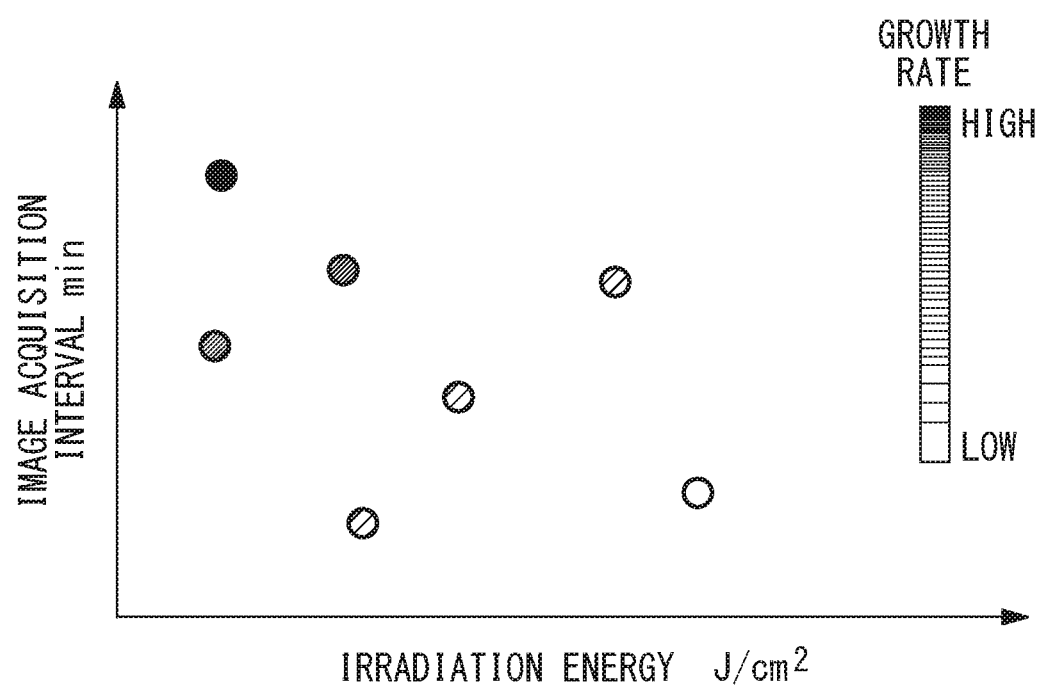
FIG. 2 shows an example assistance display generated by the observation assistance device in FIG. 1.

For example, in the example shown in FIG. 2, the assistance display includes a two-dimensional map in which the horizontal axis shows the single radiation energy and the vertical axis shows the image-capturing interval, and points generated thereon at positions corresponding to respective image-capturing conditions. The colors of the points show sample state information. The relationship between the colors of the points and the sample state information is indicated by a bar, showing legends, appearing at the side of the map.

The operations of the thus-configured observation assistance device 1 and fluorescence observation system 100 according to this embodiment will be described below.

When performing fluorescence observation of a sample using the fluorescence observation system 100 according to this embodiment, first, a user inputs the type of sample and the type of fluorescent substance via the input unit 4. Using the combination of the input sample type and fluorescent substance type, the controller 5 searches the information storage unit 3 and reads all the relevant data.

Because the thus-read data contains observation conditions and sample state information, the controller 5 generates points on a two-dimensional map, in which two preliminarily set parameters in the observation conditions are used as the coordinate axes, at positions corresponding to the observation conditions. The controller 5 sets the colors of the generated points to colors corresponding to the sample state information, generates an assistance display including a bar showing legends, and sends the assistance display to the display unit 6.

The display unit 6 displays the assistance display transmitted from the controller 5.

Specifically, the assistance display shows, by means of the points of different colors, the results of fluorescence observation performed in the past using the same sample-fluorescent substance combination as that to be used in the observation that will be performed from now. Hence, by checking the positions and colors of the points on the indicated assistance display, a user can get an idea of observation conditions that do not damage the sample in observation that will be performed from now.

For example, when the cell growth rate is indicated as the sample state information, conditions near points having a color indicating a high cell growth rate can be considered to be observation conditions that do not damage the sample. Hence, it is possible to select desired observation conditions within such observation conditions. Alternatively, when determining the single radiation energy to be used in the subsequently performed fluorescence observation, it is possible to select an image-capturing interval that does not damage the sample.

As described above, unlike the related-art technique in which invasion of the sample by excitation light is determined only by the cumulative radiation time, the fluorescence observation system 100 and the observation assistance device 1 according to this embodiment have an advantage in that it is possible to select appropriate observation conditions that do not damage the sample according to the type of sample and the type of fluorescent substance to be used, which are designated by the user, to perform fluorescence observation while maintaining the soundness of the sample.

Although it has been described that the coordinate axes of the map, serving as the assistance display, are preliminarily set in this embodiment, instead, a user may arbitrarily set the coordinate axes.

For example, as shown in FIG. 3, the coordinate axes may be arbitrarily set by selecting, using checkboxes, two parameters from a displayed list of parameters included in the observation conditions.

Although the single radiation energy and the image-capturing interval have been described as examples of the preliminarily set parameters, any parameters may be set. For example, the total radiation energy may be set instead of the single radiation energy. Because experiments show that the total radiation energy and the radiation interval are both parameters that significantly influence the state of the cells, by setting them as default coordinate axes, it is possible to more effectively suggest appropriate observation conditions to the user.

Figure 4:
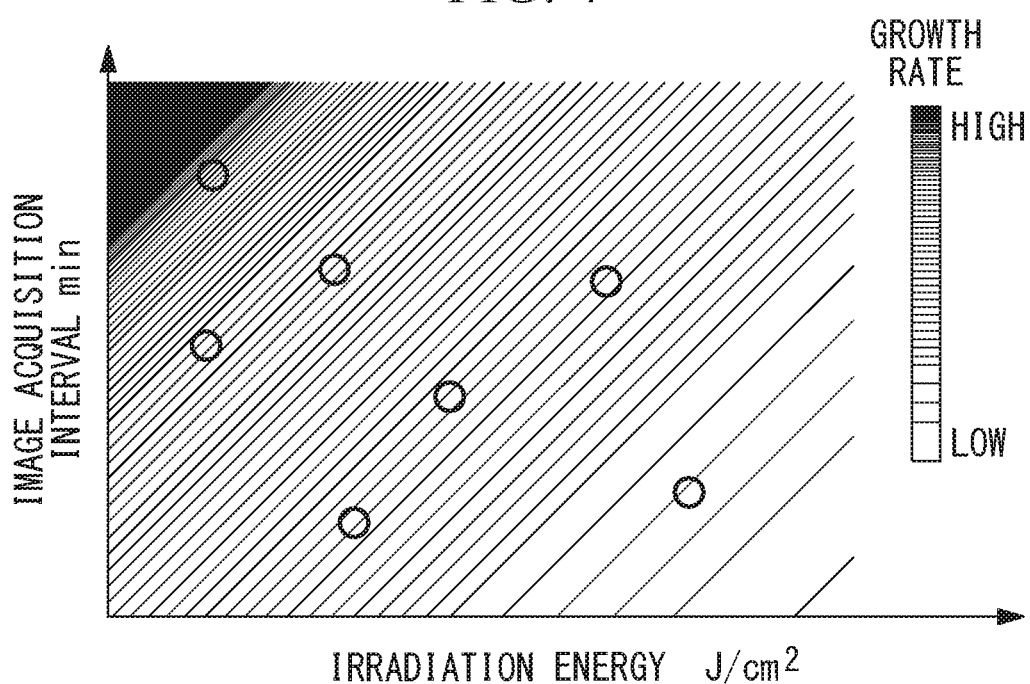
FIG. 4 shows another example assistance display generated by the observation assistance device in FIG. 1.

Although an assistance display in which two parameters in the observation conditions are used as the two coordinate axes is formed, points showing the distribution of the observation conditions are arranged, and the points are indicated with colors showing sample state information, instead, as shown in FIG. 4, an assistance display in which sample state information at positions between the points is interpolated from the positions of the points and the sample state information may be generated. By doing so, when fluorescence observation is performed under new observation conditions located between points, it is possible to more clearly and easily check, in advance, a sample state change that will occur when the fluorescence observation is performed.

In this embodiment, the sample state information under the respective observation conditions, which constitute the points in the assistance display, are generated on the basis of the results of previously performed fluorescence observation. Instead, it is possible to automatically acquire two or more sample-state-information-acquisition sample images at certain intervals while the user is performing fluorescence observation and to store this data.

In some cases, damage to the cell is detected in an image used in the fluorescence observation performed by a user, making the image unsuitable for checking the sample state. Even in such a case, the device automatically acquires sample-state-acquisition sample images suitable for checking the sample state, whereby it is possible to always accurately detect a sample state change.

Preferably, the images for acquiring the sample state are non-fluorescence images, such as phase difference images, because they will not damage the sample.

Figure 5:
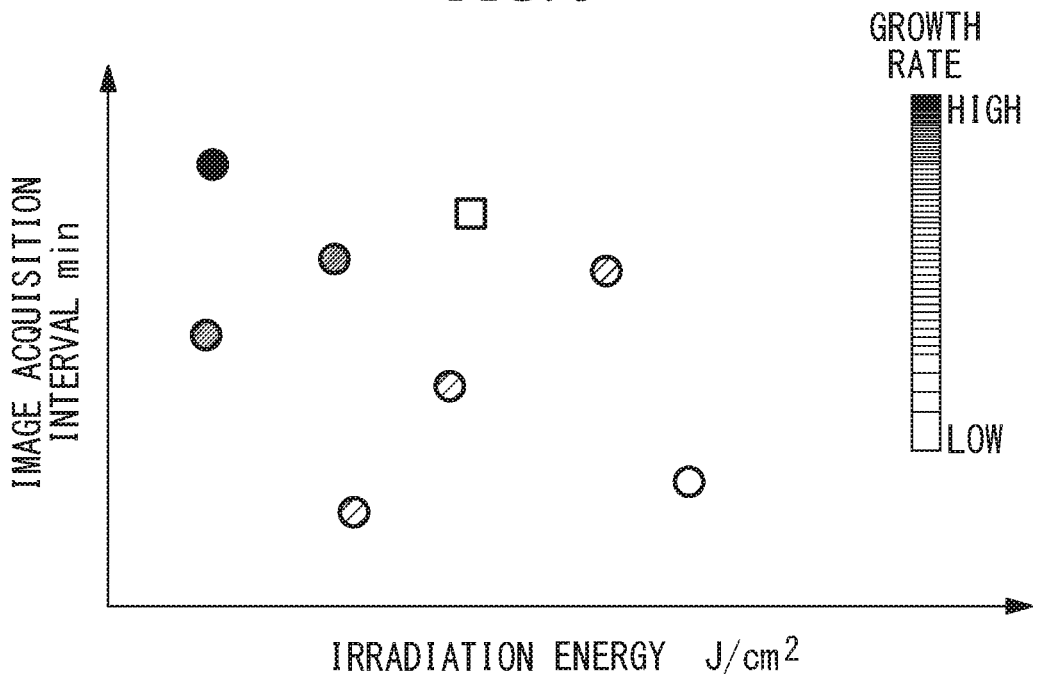
FIG. 5 shows another example assistance display generated by the observation assistance device in FIG. 1.

In this embodiment, the user inputs the type of sample and the type of fluorescent substance via the input unit 4, and the corresponding data is read and displayed. In addition to this, it is possible that the user inputs the observation conditions of the fluorescence observation to be performed next via the input unit 4, and the controller 5 generates, on the basis of the input observation conditions, a new point (for example, a rectangular point) to be included in the assistance display, as shown in FIG. 5.

Figure 6:
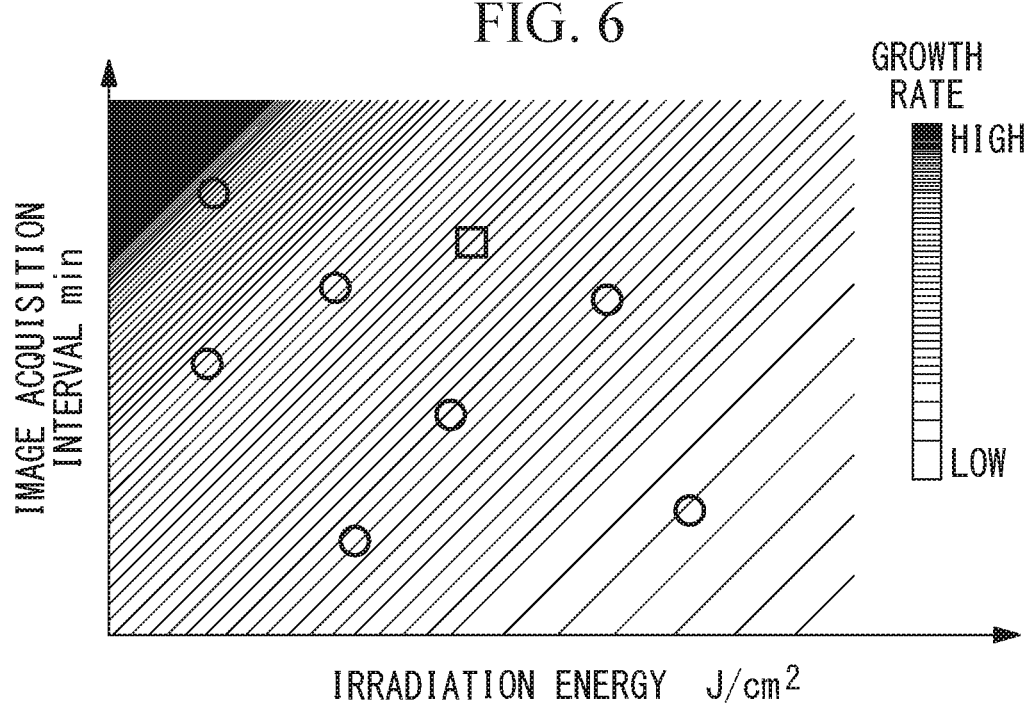
FIG. 6 shows another example assistance display generated by the observation assistance device in FIG. 1.
Figure 7:
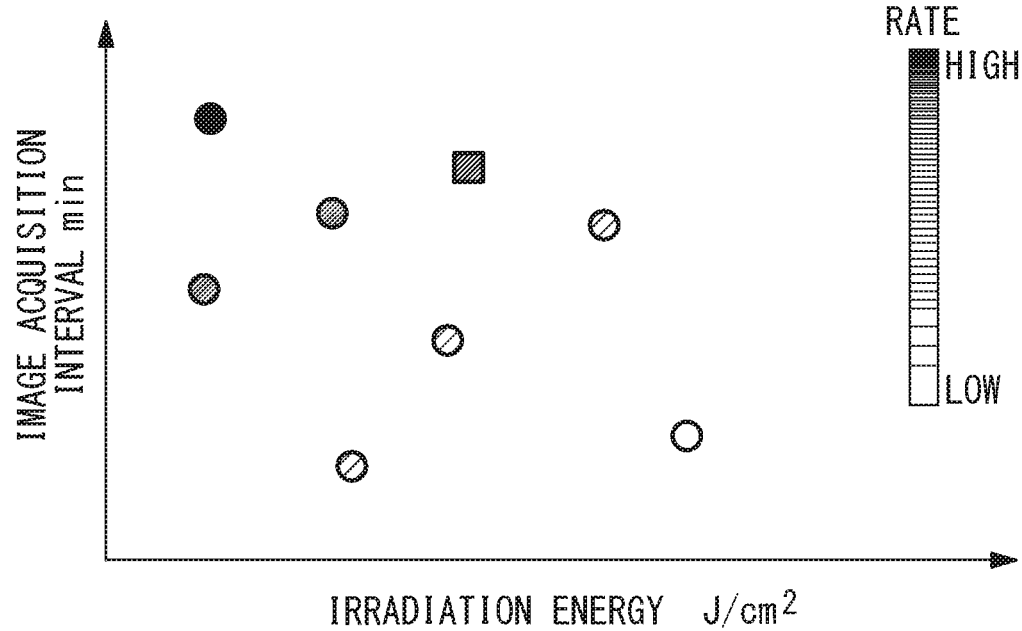
FIG. 7 shows another example assistance display generated by the observation assistance device in FIG. 1.

By doing so, a sample state change occurring in the new fluorescence observation can be checked with the generated point. As shown in FIG. 6, the new point may be generated in the interpolated assistance display in FIG. 4. As shown in FIG. 7, interpolated sample state information may be used as the color of the point. In this case, the controller 5 serves as a state forecast unit that forecasts, on the basis of past sample state information, sample state information corresponding to the conditions of an observation that is not yet performed and generates sample-state forecast information. Then, the controller 5 generates an assistance display on which the generated sample-state forecast information is superimposed.

In this embodiment, information itself that shows a sample state change, such as the growth rate, is displayed as the sample state information. Instead, whether or not the sample state information is within an appropriate range may be displayed. Herein, the appropriate range can be set to a desired range by the user.

In this case, the controller 5 serves as a determination unit that determines whether or not the sample state information is within an appropriate range and as a notification unit that displays (issues a notification of) the determination result obtained by the determination unit on the display unit.

Figure 8:
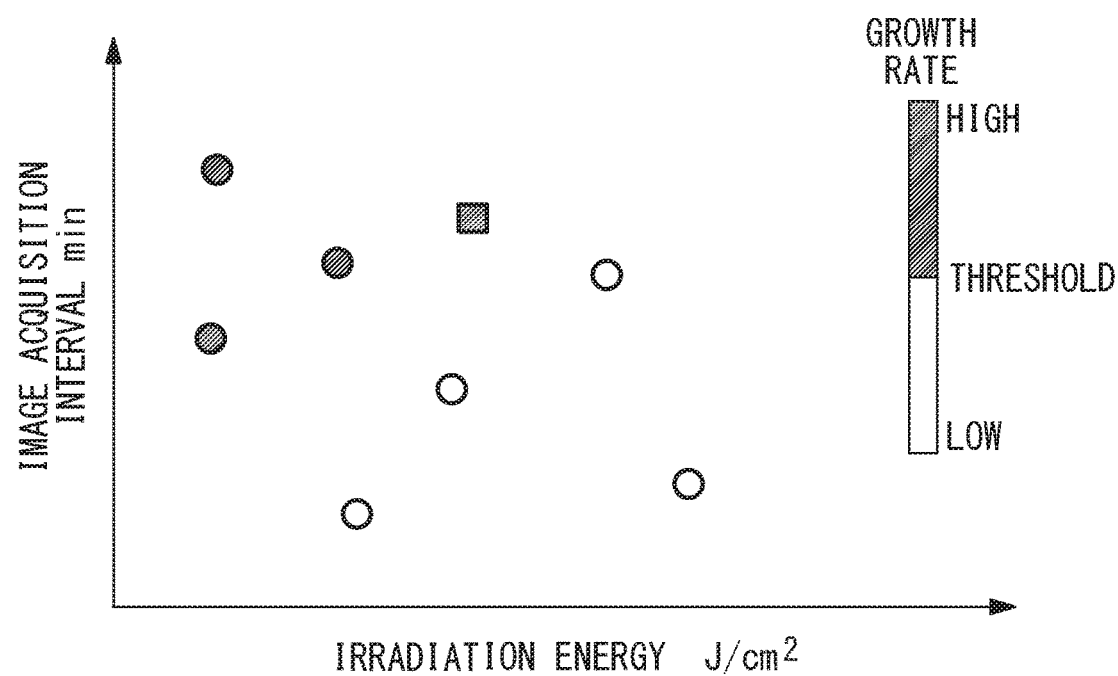
FIG. 8 shows another example assistance display generated by the observation assistance device in FIG. 1.
Figure 9:
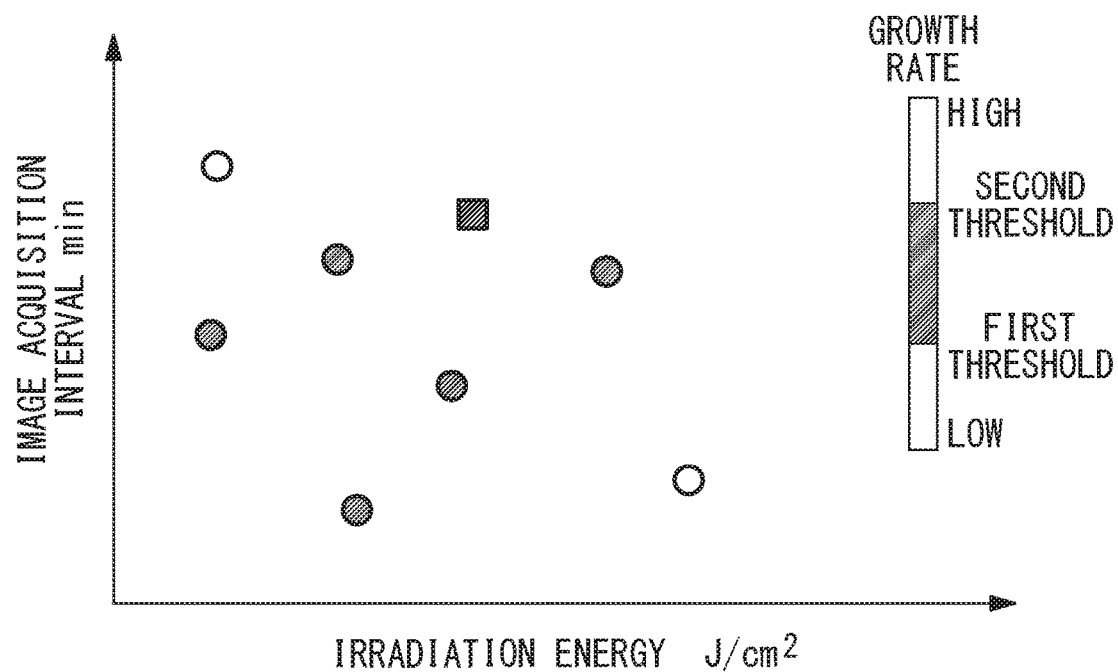
FIG. 9 shows another example assistance display generated by the observation assistance device in FIG. 1.

For example, as in the example shown in FIG. 8, the points may be colored with different colors so as to show whether or not the growth rate is higher than or equal to a predetermined threshold. As in the example shown in FIG. 9, the points may be colored with different colors so as to show whether or not the growth rate is in a range higher than the first threshold and lower than the second threshold.

This makes it easy to check whether or not the sample state information in new fluorescence observation is within the appropriate range.

In this embodiment, two parameters included in the observation conditions are selected, and a two-dimensional map, in which these parameters serve as the coordinate axes, is used as the assistance display. Instead, three or more parameters may be selected to display a three- or higher-dimensional map having three or more coordinate axes.

As a result, the following aspect is read from the above described embodiment of the present invention.

An aspect of the present invention is an observation assistance device including: an information storage unit that stores, in an associated manner, sample state information showing a sample state change, a type of sample, a type of fluorescent substance, and an observation condition in fluorescence observation performed on a predetermined sample, using a predetermined fluorescent substance, and under a predetermined observation condition including two or more parameters; an input unit via which a user inputs the type of sample to be observed and the type of fluorescent substance to be used; an assistance-display generating unit that reads, from the information storage unit, sample state information and an observation condition of fluorescence observation performed on the same type of sample as the type of sample input in the input unit, using the same type of fluorescent substance as the type of fluorescent substance input in the input unit, and generates an assistance display showing the sample state information in relation to the two or more parameters included in the observation condition; and a display unit that displays the assistance display generated by the assistance-display generating unit.

According to this aspect, when the user inputs, via the input unit, the type of sample to be observed and the type of fluorescent substance to be used, the assistance-display generating unit reads, from the information storage unit, sample state information and an observation condition of fluorescence observation performed on the same type of sample as the type of sample input, using the same type of fluorescent substance as the type of fluorescent substance input. Then, the assistance-display generating unit generates an assistance display showing the read sample state information in relation to the two or more parameters included in the read observation condition, and the generated assistance display is displayed on the display unit.

Specifically, when a user will perform observation with a new observation condition setting and inputs the type of sample and the type of fluorescent substance to be used from the input unit, observation conditions of fluorescence observation performed in the past on the same type of sample and using the same type of fluorescent substance and stored in the information storage unit are displayed in association with the sample state information showing a sample state change in this fluorescence observation. Accordingly, from the displayed relationship between the sample state information and the observation conditions, it is possible to allow a user to forecast a sample state change that will occur in fluorescence observation to be performed from now. Thus, it is possible to assist a user in selecting an observation condition under which low-invasion fluorescence observation can be performed.

In the above aspect, the observation assistance device may further include an image analysis unit that analyzes an image acquired in the fluorescence observation performed on the predetermined sample, using the predetermined fluorescent substance, under the predetermined observation condition including the two or more parameters and extracts the sample state information.

With this configuration, the image analysis unit analyzes an image acquired in the fluorescence observation performed on the predetermined sample, using the predetermined fluorescent substance, and extracts the sample state information. The extracted sample state information is stored in the information storage unit in association with the type of sample, the type of fluorescent substance, and the observation condition so as to be used in future observation. Specifically, by using an image acquired in the fluorescence observation performed by the user, the sample is not needlessly irradiated with the excitation light, and thus, it is possible to maintain the sample in a sound state.

In the above aspect, two or more sample-state-information-acquisition sample images may be acquired at a certain interval, while a plurality of images are acquired in the fluorescence observation performed on the predetermined sample, using the predetermined fluorescent substance, under the predetermined observation condition including the two or more parameters.

With this configuration, it is possible to always accurately detect a sample state change.

In the above aspect, the two or more sample-state-information-acquisition sample images acquired at a certain interval may be non-fluorescence images.

With this configuration, it is possible to reduce damage to the sample.

In the above aspect, the assistance-display generating unit may generate an assistance display in which the sample state information under the respective observation conditions is superimposed on a map in which the two or more parameters are used as the coordinates, the map showing the distribution of the respective observation conditions.

With this configuration, the sample state information is superimposed on the map showing the distribution of the observation conditions, the map being shown on the display unit. As a result, it is possible to easily allow a user to visually understand the extent of the sample state information under a new observation condition.

In the above aspect, the input unit may allow the user to input a new observation condition, and the assistance-display generating unit may generate the assistance display in which information showing the position of the thus-input new observation condition is added on the map.

With this configuration, the information showing the position of the new observation condition input by the user via the input unit is added on the map. Hence, it is possible to allow the user to visually understand, at a glance, the extent of the sample state information under the new observation condition.

In the above aspect, the observation assistance device may further include a state forecast unit that generates sample-state forecast information, which is a forecast of the sample state information corresponding to the condition of an observation that is not yet performed, on the basis of the sample state information under the respective observation conditions read from the information storage unit. The assistance-display generating unit may generate an assistance display on which the sample-state forecast information generated by the state forecast unit is superimposed.

With this configuration, the sample state information corresponding to the condition of observation that is not yet performed, which is generated by the state forecast unit, is included in the assistance display. Hence, it is possible to more quantitatively check a sample state change occurring in a new fluorescence observation.

In the above aspect, the observation assistance device may further include: a determination unit that determines whether or not the sample state information indicated on the assistance display is within an appropriate range; and a notification unit that notifies the determination result obtained by the determination unit. This appropriate range can be set to a desired range by a user.

With this configuration, it is possible to easily check, from the determination result notified by the notification unit, whether or not the sample state information showing a sample state change occurring in new fluorescence observation is within an appropriate range.

Another aspect of the present invention is a fluorescence observation system including: an image acquisition unit that acquires a fluorescence image under a prescribed observation condition, on a predetermined sample, and using a predetermined fluorescent substance; and any one of the observation assistance devices described above.

REFERENCE SIGNS LIST 1 observation assistance device
2 image analysis unit
3 information storage unit
4 input unit
5 controller (assistance-display generating unit, state forecast unit, determination unit, notification unit)
6 display unit
100 fluorescence observation system
110 microscope (image acquisition unit)

The invention claimed is:

1. An observation assistance device comprising:
   an information storage unit that is configured to store, in an associated manner, sample state information showing a sample state change, a type of sample, a type of fluorescent substance, and an observation condition in fluorescence observation performed on a predetermined sample, using a predetermined fluorescent substance, and under a predetermined observation condition including two or more parameters;
   an input unit via which a user inputs the type of sample to be observed and the type of fluorescent substance to be used;
   an assistance-display generating unit that is configured to generate an assistance display showing the sample state information on the basis of the type of sample and the type of fluorescent input in the input unit; and
   a display unit that is configured to display the assistance display generated by the assistance-display generating unit, wherein
   the assistance-display generating unit comprises a one or more processor,
   the processor is configured to read, from the information storage unit, sample state information and an observation condition of fluorescence observation performed on the same type of sample as the type of sample input in the input unit, using the same type of fluorescent substance as the type of fluorescent substance input in the input unit, and generates the assistance display in relation to the two or more parameters included in the observation condition.

2. The observation assistance device according to claim 1, further comprising an image analysis unit that analyzes an image acquired in the fluorescence observation performed on the predetermined sample, using the predetermined fluorescent substance, under the predetermined observation condition including the two or more parameters and extracts the sample state information.

3. The observation assistance device according to claim 1, wherein two or more sample-state-information-acquisition sample images are acquired at a certain interval while a plurality of images are acquired in the fluorescence observation performed on the predetermined sample, using the predetermined fluorescent substance, under the predetermined observation condition including the two or more parameters.

4. The observation assistance device according to claim 3, wherein the two or more sample-state-information-acquisition sample images acquired at a certain interval are non-fluorescence images.

5. The observation assistance device according to claim 1, wherein the processor is configured to generate an assistance display in which the sample state information under the respective observation conditions is superimposed on a map in which the two or more parameters are used as the coordinates, the map showing the distribution of the respective observation conditions.

6. The observation assistance device according to claim 5, wherein
   the input unit allows the user to input a new observation condition, and
   the processor is configured to generate the assistance display in which information showing the position of the thus-input new observation condition is added on the map.

7. The observation assistance device according to claim 1, further comprising a state forecast unit that is configured to generate sample-state forecast information, which is a forecast of the sample state information corresponding to the condition of an observation that is not yet performed, on the basis of the sample state information under the respective observation conditions read from the information storage unit, wherein the processor is configured to generate an assistance display on which the sample-state forecast information generated by the state forecast unit is superimposed.

8. The observation assistance device according to claim 1, further comprising:
- a determination unit that is configured to determine whether or not the sample state information indicated on the assistance display is within an appropriate range; and
- a notification unit that is configured to notify the determination result obtained by the determination unit.

9. A fluorescence observation system comprising:
- an image acquisition unit that is configured to acquire a fluorescence image under a prescribed observation condition, on a predetermined sample, and using a predetermined fluorescent substance; and
- the observation assistance device according to claim 1.

* * * * *